(12) United States Patent
Serai et al.

(10) Patent No.: US 7,911,595 B2
(45) Date of Patent: Mar. 22, 2011

(54) LIQUID FUEL PROPERTY DETECTION SYSTEM

(75) Inventors: Tetsuro Serai, Anjo (JP); Kazuki Matsuo, Okazaki (JP); Hiroshi Nakamura, Nishio (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 0 days.

(21) Appl. No.: 12/626,723

(22) Filed: Nov. 27, 2009

(65) Prior Publication Data

US 2010/0157302 A1    Jun. 24, 2010

(30) Foreign Application Priority Data

Dec. 18, 2008    (JP) ................................. 2008-322918

(51) Int. Cl.
*G01N 33/28*    (2006.01)
(52) U.S. Cl. ........................................................ 356/70
(58) Field of Classification Search ................... 356/70, 356/432, 433, 435
See application file for complete search history.

(56) References Cited

U.S. PATENT DOCUMENTS

| | | | |
|---|---|---|---|
| 4,570,069 A * | 2/1986 | Gager | 250/343 |
| 2004/0036855 A1 * | 2/2004 | Hammer et al. | 356/70 |
| 2008/0246955 A1 | 10/2008 | Osaki et al. | |
| 2008/0319685 A1 * | 12/2008 | Xie et al. | 702/45 |

* cited by examiner

*Primary Examiner* — Roy Punnoose
(74) *Attorney, Agent, or Firm* — Nixon & Vanderhye PC

(57) ABSTRACT

A liquid fuel property detection apparatus includes a fuel passage, a light emitting device for emitting a light including a plurality of predetermined wavelengths toward the fuel in the passage, a light receiving device for receiving the light passing through the fuel, and a calculation unit for calculating the concentration of at least one of aroma, paraffin and olefin, which are hydrocarbon component components contained in the fuel. The calculation unit calculates the concentration of a specific component, which is one of aroma, paraffin and olefin, based on the reference transmittance of light in the specific component and the actual transmittance calculated from the amount of light emitted by the light emitting device and the amount of light received by the light receiving device with respect to each wavelength of the light.

8 Claims, 4 Drawing Sheets

LIQUID FUEL PROPERTY DETECTION SYSTEM

CROSS REFERENCE TO RELATED APPLICATION

This application is based on and incorporates herein by reference Japanese Patent Application No. 2008-322918 filed on Dec. 18, 2008.

FIELD OF THE INVENTION

The present invention relates to a liquid fuel property detection apparatus for detecting the property of liquid based on the light transmitting property of the liquid.

BACKGROUND OF THE INVENTION

In a conventional liquid fuel property detection apparatus (for example, patent documents 1 and 2), a light beam emitted by a light emitting device is irradiated into fuel, the light beam transmitted through the fuel is received by a light receiving device, and the concentration of a specific component contained in the fuel is detected based on the amount of received light beam and the like.

In the first conventional technology according to patent document 1, a sensor having a light source is provided. The light source emits a light beam toward fuel flowing in a measurement cell to be supplied to an engine. The light beam emitted from the light source is separated by a semi-reflective separation plate into a light beam reflected by the semi-reflective separation plate and a light beam transmitted through the semi-reflective separation plate. The reflected light beam passes through the fuel in the measurement cell and enters a photo transistor (light receiving element) after being absorbed and attenuated by the fuel. The transmitted light beam, which passed through the semi-reflective separation plate, arrives at the other photo transistor (light receiving element) after being attenuated when passing through the other cell containing a reference fuel (for example, pure methanol). The property of fuel is determined based on a difference between rates of attenuation of the light beams by these cells.

In the second conventional technology according to patent document 2, two light beams of different wavelengths are irradiated to fuel containing a plurality of predetermined components and the concentration of only a specific component is detected based on the transmittance of each light beam. In the second conventional technology, more specifically, the two light beams irradiated toward fuel containing three components of gasoline, ethanol and water are a first wavelength light beam and a second wavelength light beam. The first wavelength light beam has a large difference between light transmittances relative to gasoline and to the remaining components. The second wavelength light beam has a large difference between light transmittances relative to water and the remaining components. The amount of transmission of each light beam in the fuel is measured. The water concentration in the fuel is detected based on the amount of light transmission of the second wavelength light beam. The ethanol concentration in the fuel is detected based on the amount of transmission of the first wavelength light beam and the detected water concentration.

Patent document 1: JP 59-210345A (U.S. Pat. No. 4,594,968)
Patent document 2: JP 2008-281546A (US 2008/0246955A)

Fuel contains hydrocarbon series components (for example, aroma, olefin, paraffin and the like), which are different in bonding state but similar in molecular configuration with respect to carbon. It is technically valuable from the standpoint of, for example, improving fuel economy and exhaust emission of an internal combustion engine, to individually detect such similar hydrocarbon series components.

According to the first conventional technology, it is possible to detect a component, which absorbs only a specific wavelength. However, if it is desired to individually detect similar hydrocarbon components, the light absorption characteristic of each component interfere one another. For this reason, it is not possible to individually detect the similar hydrocarbon components by using a light beam of only one wavelength.

According to the second conventional technology, it is possible to detect the concentrations of three components, gasoline, ethanol and water, which are largely different in molecular configuration.

SUMMARY OF THE INVENTION

It is therefore an object of the present invention to provide a liquid fuel property detection apparatus, which can detect a specific component in similar hydrocarbon series substance.

According to one aspect of the present invention, a liquid fuel property detection apparatus is provided with a fuel passage, a light emitting device, a light receiving device and a calculation unit. The light emitting device emits a light including a plurality of predetermined wavelengths toward fuel in the passage transversely. The light receiving device receives the light including the plurality of predetermined wavelengths through the fuel. The calculation unit calculates concentration of at least one specific component of aroma component, paraffin component and olefin component, which are hydrocarbon series constituent substances contained in the fuel. The calculation unit calculates the concentration of a specific component of at least one of the aroma component, the paraffin component and the olefin component based on a characteristic of reference transmittance of the light in the specific component and actual transmittance of the light, which is calculated from an amount of the light including the plurality of predetermined wavelengths emitted from the light emitting device and an amount of the light received by the light receiving device. The reference transmittance and the actual transmittance are related to the plurality of predetermined wavelengths.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

The present invention is described in more detail with reference to various embodiments, in which the same or similar parts are denoted by the same or similar reference numerals or symbols.

First Embodiment

Figure 1:
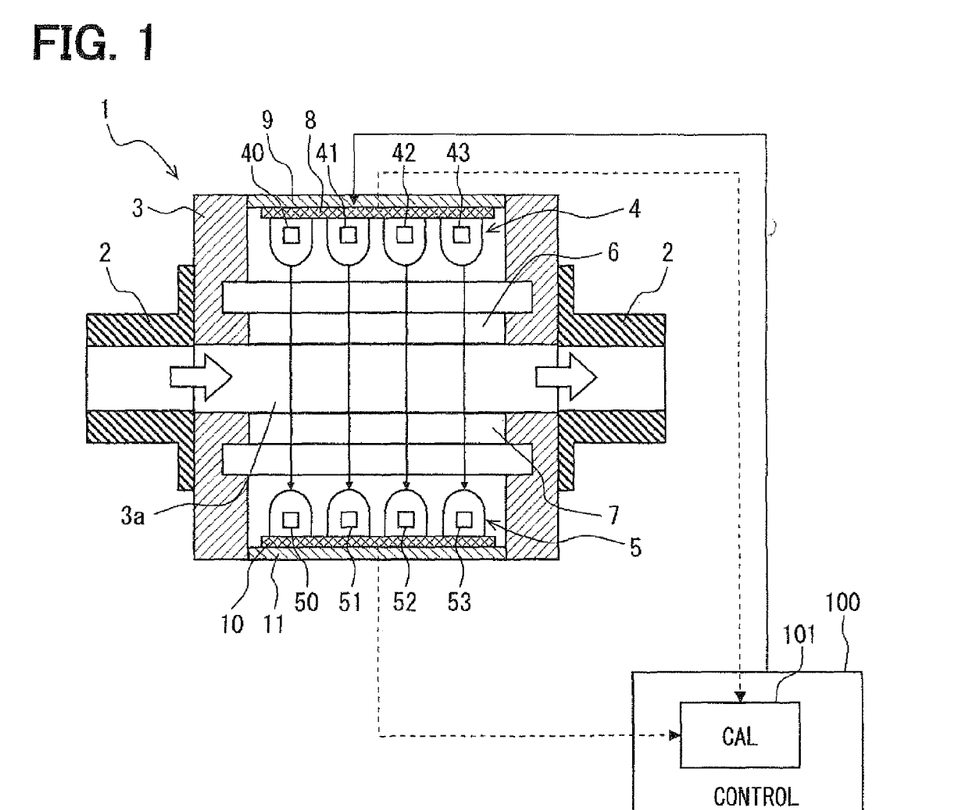
FIG. 1 is a schematic diagram showing a liquid fuel property detection apparatus according to the first embodiment of the present invention.

Referring to FIG. 1, a liquid fuel property detection apparatus is provided with a fuel property sensor 1 and an electronic control unit 100, which detect a specific hydrocarbon component in liquid fuel supplied to an engine in an engine control system of a vehicle.

The engine control system has a fuel pipe 2 for supplying fuel under control of the control unit 100 and other parts (not shown). The control unit 100 includes a central processing unit (CPU) 101 as a calculation unit, an input circuit for receiving various signals and an output circuit for outputting signals to drive various actuators, so that fuel injection amount, fuel injection time, spark ignition time, throttle valve position, and the like are controlled. The control unit 100 also includes memories such as a ROM, a RAM and the like, which store calculation programs, control programs and the like, which are executed by calculation unit 101.

Gasoline, which is liquid fuel for the engine, includes a variety of hydrocarbon series components. The hydrocarbon components in gasoline are generally grouped into an aroma component, an olefin component and a paraffin component. The aroma component includes aromatic hydrocarbons having benzene nucleus. The olefin component includes chain hydrocarbons, each of which has one double-bond. The paraffin component includes chain hydrocarbons, which do not have unsaturated bond and ring configuration. The fuel property sensor 1 is used to detect the concentration of at least one specific component among aroma component, olefin component and paraffin component, which are hydrocarbon component constituent substances contained in liquid fuel.

The fuel property sensor 1 is interposed in the fuel pipe 2, which supplies fuel from a fuel tank (not shown) to the engine, in such a manner that fuel flows in the fuel property sensor 1. The fuel property sensor 1 is electrically connected to the control unit 100. The control unit 100 controls emission of inspection light beam provided for detecting a specific component in gasoline. The control unit 100 receives the wavelength and the amount of emitted light beam as well as the amount of light beam received after passing through the gasoline.

In the fuel property sensor 1, a light emitting device 4 and a light receiving device 5 are accommodated within a body 3 having a fuel passage 3*a*, in which fuel flows. The light emitting device 4 is disposed to emit light beams into fuel flowing in the passage 3*a* transversely. The light receiving device 5 is disposed to receive the light beams, which have transversely passed through the fuel in the passage 3*a*.

The body 3 may be formed of a non-transparent substance, for example, metal or resin. The passage 3*a* is formed in the radial center of the body 3 to pass through both axial ends of the body 3. The passage 3*a* is coupled to the fuel pipe 2 at its both axial ends. The fuel is assumed to flow from the fuel tank to the engine in a direction indicated by large arrows in FIG. 1.

In the body 3, a pair of light conducting plates 6 and 7 is provided in a manner to face each other and sandwich the passage 3*a* therebetween. The light conducting plate 6 is provided to define a part of the passage 3*a* and conducts the light beams emitted from the light emitting device 4 therethrough to be irradiated into the passage 3*a* as shown by small arrows in the figure. The light conducting plate 7 is provided to define a part of the passage 3*a* and conducts the light beams passing through the passage 3*a* to the light receiving device 5 as shown by the small arrows in the figure.

The light emitting device 4 is configured to emit a plurality of light beams of different wavelengths toward the fuel in the passage 3*a*. The wavelengths may be in the near-infrared range (700 nm to 2,400 nm). The light emitting device 4 includes a plurality of light emitting elements 40 to 43, specifically diodes. The number of the light emitting elements may be the same as or different from the number of wavelengths of the emitted light beams. In summary, the light emitting device 4 is configured to be able to emit light, which includes all of a plurality of light beams of predetermined wavelengths irrespective of the number of light emitting elements.

The number of the light emitting elements of the light emitting device 4 is four, which is the same as the number of light receiving elements of the light receiving device 5. The four light emitting elements are a first light emitting element 40, a second light emitting element 41, a third light emitting element 42 and a fourth light emitting element 43, which emit respective light beams of different wavelengths. Each light emitting element 40 to 43 has a light collecting part, which collects emitted light. The light emitting elements 40 to 43 emit a first wavelength light beam, a second light wavelength light beam, a third wavelength light beam and a fourth wavelength light beam, which have respective wavelengths different one another. The light emitting elements 40 to 43 emit light beams of the first wavelength, the second wavelength, the third wavelength and the fourth wavelength, respectively, as the center frequencies at which the luminance is the highest. Each of the light emitting elements 40 to 43 also emits light beams of other wavelengths, which is near its center wavelength. Each light emitting element 40 to 43 outputs a signal, which indicates the amount of light beam emitted by itself, to the calculation unit 101.

The light receiving device 5 is configured to receive the light beams emitted from the light emitting device 4 and transmitted through the fuel in the passage 3*a*. The light receiving device 5 includes a plurality of light receiving elements 50 to 53, which receive light beams of wavelengths in the near-infrared range (700 nm to 2,400 nm). The light receiving device 5 may be photo diodes. The number of the light receiving elements may be the same as or different from the number of wavelengths of the light beams emitted by the light emitting device 4. In summary, the light receiving device 5 is configured to be able to receive light beams, which include all of a plurality of light beams of predetermined wavelengths irrespective of the number of light receiving elements.

The number of the light receiving elements of the light receiving device 5 is four, which is the same as the number of the light emitting elements 40 to 43 of the light emitting device 4. The four light receiving elements are a first light receiving element 50, a second light receiving element 51, a third light receiving element 52 and a fourth light receiving element 53, which receive respective light beams of different wavelengths. The light receiving elements 50 to 53 have different peak sensitivities one another with respect to the wavelength of light beam thereby to selectively receive light beams of the predetermined wavelengths. The light receiving elements 50 to 53 are configured to selectively receive the light beams of the first wavelength, the second wavelength, the third wavelength and the fourth wavelength emitted by the light emitting elements 40 to 43, respectively. Each light receiving element 50 to 53 outputs a signal, which indicates the amount of light beam received by itself, to the calculation unit 101.

The light emitting elements 40 to 43 and the light receiving elements 50 to 53 are all chip type elements. The light emitting elements 40 to 43 are mounted on a circuit substrate 8. The light receiving elements 50 to 53 are mounted on a circuit substrate 10. The circuit substrates 8 and 10 are connected to external electric wires through an electric connector and further to the control unit 100 through the external electric wires. The light emitting elements 40 to 43 are driven to emit respective light beams of the first to the fourth wavelengths. The output signals of the light receiving elements 50 to 53 are applied to the control unit 100.

Covers 9 and 11 are attached to the body 3 at the side of the light emitting device 4 and at the side of the light receiving device 5, respectively. The covers 9 and 11 are made of metal, resin or the like material, to protect the light emitting elements 40 to 43 and the light receiving elements 50 to 53 with required fluid tightness.

Figure 2:
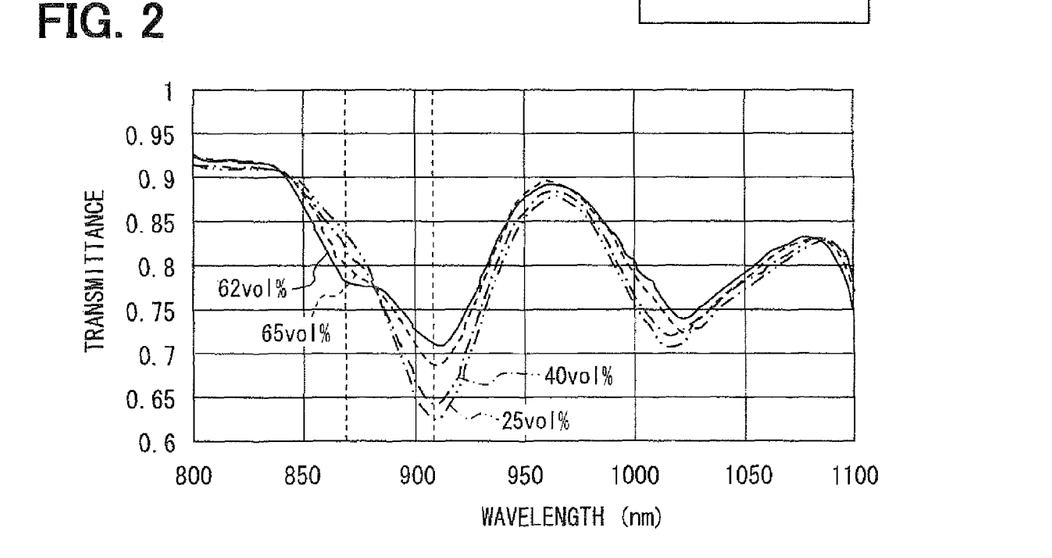
FIG. 2 is a graph showing a relation between the wavelength and transmittance of light in aroma component in liquid fuel.

The method of detecting the concentration of a specific component such as aroma component by the fuel property sensor 1 is described next. FIG. 2 shows a relation between the wavelength of a light beam and the reference transmittance of the beam in liquid fuel including aroma component, which is a specific component.

As understood in FIG. 2, the reference transmittances of light beams relative to the wavelengths vary in accordance with the concentration of the aroma component, for example, 25 vol % (chain double-dashed line), 40 vol % (chain line), 62 vol % (solid line), and 65 vol % (broken line). The transmittance spectrum of each volume percentage (vol %) has a unique wavelength (peak wavelength), at which the transmittance presents a peak value, and the transmittance at the peak wavelength. The calculation unit 101 calculates the concentration (vol %) of aroma component in liquid fuel based on such a reference characteristic between wavelength and transmittance and an actually calculated transmittance.

As shown in FIG. 2, the reference transmittance presents the lowest peak in the wavelength range from 900 nm to 920 nm with respect to each concentration of aroma component. This is because light beam is absorbed in the bond between C and H in the molecular configuration of fuel. If atomic element C of CH is double-bonded, the range of peak wavelength is likely to shift to the shorter wavelength side (left side in FIG. 2). As a result, the light beam is absorbed and the transmittance decreases in the wavelength range between 860 nm and 870 nm. The light beam is also absorbed remarkably in another wavelength range between 1010 nm and 1025 nm and hence the transmittance presents another local minimum value. Based on the characteristics shown in FIG. 2, it is possible to detect the aroma component of 62 vol % or 65 vol %, which includes more double-bonds, by separating from the aroma component of 25 vol % and 40 vol %. Thus, the concentration of aroma component in fuel can be detected accurately. It is further possible to detect individually the aroma component, which has more double-bonds, the olefin component and the paraffin component among the specified components.

The predetermined wavelengths of the light beams emitted by the light emitting elements 40 to 43 are the wavelengths preselected from among the wavelengths, at which the transmittance attains the peak values shown in FIG. 2, for example. By thus selecting the predetermined wavelengths, which present the characteristic transmittances, to detect the property of fuel, the concentration of the specific component to be detected can be detected with high accuracy.

The olefin component and the paraffin component also have individual characteristics depending on different concentrations as in the case of the aroma component. These individual characteristics are stored in the ROM or the like in the control unit 100, so that the concentration of at least one component of aroma, olefin and paraffin may be calculated by using the stored individual characteristic of the specific component and the actually calculated transmittance. That is, the concentration of the specific component can be determined by comparing the calculated transmittance with the stored characteristic values of transmittance.

The concentration of the specific component in at least one of aroma component, olefin component and paraffin component in fuel is detected in the following manner by using the liquid fuel property detection apparatus. When an ignition (not shown) is turned on to start the engine by a driver, the control unit 100 starts its operation so that the engine control system becomes operative. The control unit 100 is configured to perform a routine of detecting the specific component in fuel as one of a plurality of control routines required to control the engine.

When the specific component detection routine is started, the control unit 100 performs an initialization process and drives the light emitting diodes 40 to 43 to emit respective light beams of the predetermined different wavelengths. The calculation unit 101 calculates the transmittances of the light beams in fuel based on the amounts of light beams received by the light receiving elements 50 to 53 and indicated by the detection signals of the light receiving elements 50 to 53. The calculation unit 101 calculates the concentration of the specific component based on the transmittances of the light beams calculated with respect to each of the predetermined wavelengths of the emitted light beams. The following method of calculation of concentration is one example, which uses prestored mathematical equations, performed based on the characteristic curves between the wavelength and the transmittance of light beam as well as the transmittance actually calculated.

Each light emitting element 50 to 53 receives the light beam of the predetermined wavelength corresponding to the specific component, which is to be detected, and outputs its detection signal to the calculation unit 101. The detection signal varies with the received light amount I(n). "n" is 1, 2, 3, or 4, which identifies the particular one (first, second, third and fourth) of the four light receiving elements 50 to 53. I(n) therefore indicates the amount of light received by the n-th one of the light receiving elements 50 to 53. The calculation unit 101 calculates the transmittance T(n) based on the following equation (Eq. 1).

$$T(n)=I(n)/Io(n) \quad \text{(Eq. 1)}$$

"Io(n)" indicates the amount of light emitted by the n-th one of the light emitting elements 40 to 43.

The concentration P of the specific component is calculated based on the following equation (Eq. 2), which is a function of the transmittance T(n).

$$P = f(T(1), T(2), \ldots, T(n)) \quad \text{(Eq. 2)}$$

The control unit 100 pre-stores the following equation (Eq. 4), which is one example of equations corresponding to the equation (Eq. 2). The concentration P of the specific component is determined by substituting the calculated transmittances T(1), T(2), . . . , T(n) of respective wavelengths in equation (Eq. 4).

The equation (Eq. 4) is determined by multivariate analysis technique. It is a prediction relation, which uses the transmittances of the light beams of the predetermined wavelengths as explaining variable and uses the predetermined concentration (fuel property) of the specific component as object variable. It is assumed that the concentration (fuel property) of the specific component is expressed as the following first-order (linear) equation (Eq. 3) of transmittance Ti. Here, "i" is a predetermined wavelength (nm), which is preselected as very influential in detection of the specific component. "Ti" is therefore the transmittance of light having the wavelength i.

$$P0 = a0 + a1 \times T810 + a2 \times T820 + \ldots + an \times Ti \quad \text{(Eq. 3)}$$

By the multiple linear regression analysis of the equation Eq. 3, the following equation Eq. 4 is derived by the wavelength, which is most influential to determine the concentration of the predetermined specific component, and the partial regression coefficient.

$$P = A0 + A4 \times T840 + A8 \times T880 + A12 \times T920 \quad \text{(Eq. 4)}$$

A0 is a constant term, and A4, A8 and A12 are predetermined constants.

According to the equation Eq. 4, the concentration P of the predetermined specific component is readily calculated by the first-order calculation, that is, by substituting the calculated actual three transmittances T840, T880 and T920 in the equation Eq. 4. The three transmittances are calculated based on the amounts of light beams of three wavelengths, 840 nm, 880 nm, 920 nm emitted from the light emitting device 4 toward fuel and the amounts of light beams received by the light receiving device 5. It is noted in FIG. 2 that the transmittances T840 at wavelength 840 nm and T880 at wavelength 880 nm are generally the same even if the concentration are different, but the transmittances T920 at wavelength 920 nm remarkably vary depending on the concentrations.

In case that the number of specific components to be detected is plural, the control unit 100 is configured to store a prediction relation like the equation Eq. 4 for each of the specific components. The liquid fuel property detection apparatus determines the concentration of each specific component by substituting transmittances calculated by the calculation unit 101 for the prediction relation by using a plurality of wavelengths corresponding to the stored prediction relation.

The liquid fuel property detection apparatus has the following operation and advantage. The fuel property sensor 1 is provided with the fuel passage 3a, in which fuel flows, the light emitting device 4 for emitting light including light beams of a plurality of predetermined wavelengths toward the fuel in the passage 3a, the light receiving device 5 for receiving the light beams of the plurality of wavelengths and transmitted through fuel, and the calculation unit 101 for calculating the concentration of at least one of aroma component, paraffin component and olefin component, which are hydrocarbon series constituent substances contained in the fuel. The calculation unit 101 calculates the concentration of the specific component of at least one of the aroma component, the paraffin component and the olefin component based on the characteristic of reference transmittance of the specific component relative to wavelength and the actual transmittance, which is calculated from an amount of the light emitted from the light emitting device 4 and including the light beams of the plurality of wavelengths and the amount of the light beams received by the light receiving device 5.

According to the fuel property sensor 1, light beams of a plurality of predetermined wavelengths is emitted to fuel, and the concentration of the specific component of fuel to be detected is calculated based on the transmittance of light calculated by the calculation unit 101 and a specific relation between the wavelength and the transmittance. This relation is variable with the volume concentration in the aroma component, the paraffin component and olefin component in the fuel. As a result, the volume concentration of the specific component to be detected can be determined accurately. It is thus possible to provide the liquid fuel property detection apparatus, which can accurately detect the specific component in the similar hydrocarbon series substances contained in fuel.

The control specifications for an engine greatly vary with the percentage of the specific component, which greatly influences the octane rating or volatility of gasoline. Therefore it is essential from the standpoint of engine performance and global environment to perform optimum control. By thus measuring accurately the aroma component, paraffin component, the olefin component, etc. individually, details of control parameters for optimizing the engine performance such as cleaning exhaust emission and realization of fuel economy can be set appropriately.

The calculation unit 101 calculates the concentration of the specific component of at least one of the aroma component, the paraffin component and olefin component by substituting the calculated transmittance for the prediction relation. This relation is determined based on the characteristic of transmittance relative to the wavelength regarding the specific component by using the multivariate analysis technique. Specifically, the calculation unit 101 reads out the characteristic and the prediction relation from the memory. The characteristic indicates the relation between the wavelength and the transmittance with respect of the specific component to be detected. The prediction relation for calculating the concentration of the specific component is determined by using the multivariate analysis technique.

According to this calculation technique, in calculating the concentration of the specific component, the prediction relation simplified by using the multivariate analysis technique is used. In this case, each of the predetermined wavelengths having great influence is the explanation variable and the concentration of the specific component is the object variable. As a result, in comparison to the case in which the calculation is performed by using a stored characteristic map, etc., the volume of memory can be reduced and the volume of calculation by the calculation unit 101 can be reduced.

Second Embodiment

Figure 3:
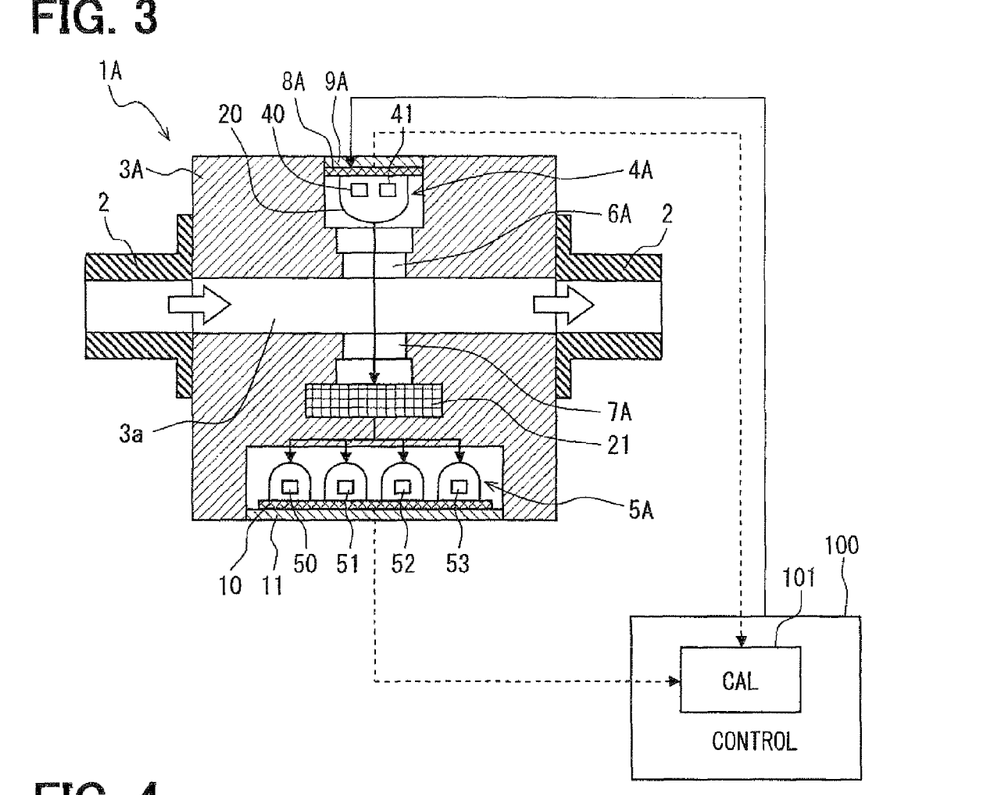
FIG. 3 is a schematic diagram showing a liquid fuel property detection apparatus according to the second embodiment of the present invention.

A fuel property sensor 1A according to the second embodiment is shown in FIG. 3. In the second embodiment, a light emitting device 4A and a light receiving device 5A of the fuel property sensor 1A are configured to have the light emitting spectrum and the light reception spectrum, which are shown in FIG. 4 in a simplified form.

In the fuel property sensor 1A, the light emitting device 4A includes a plurality of (two) light emitting elements (first light emitting element 40, second light emitting element 41), which are less in number than light receiving elements 50 to 53 in the light receiving device 5A. The light emitting device 4A further includes a light combining device 20, which produces composite light by combining the light beams of the light emitting elements 40 and 41. A light separating device 21 is provided between the passage 3a and the light receiving device 5A, so that the composite light having passed through the fuel is separated into a plurality of light beams to be received by a plurality of light receiving elements (first light receiving element 50, second light receiving element 51, third light receiving element 52 and fourth light receiving element 53), respectively as shown by fine arrows.

The light emitting device 4A is so configured that the first light emitting element 40 and the second light emitting element 41 emit respective light beams and the light combining device 20 combines these light beams into the composite light. The light combining device 20 may be a light collecting lens, which covers the front parts of the first light emitting element 40 and the second light emitting element 41 at a side of a light conducting plate 6A. The first light emitting element 40 and the second light emitting element 41 are configured to emit respective light beams of predetermined wavelengths. Alternatively, each of the first light emitting element 40 and the second light emitting element 41 may emit a light beam of a single predetermined wavelength or a plurality of predetermined wavelengths.

Figure 4:
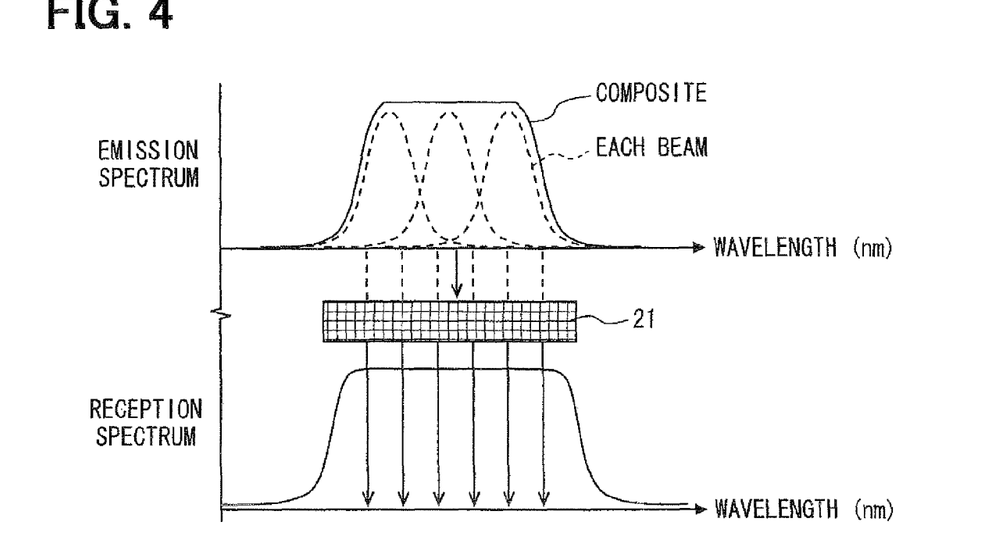
FIG. 4 is an illustration of the light emission spectrum of a light emitting device and the light reception spectrum of a light receiving device in the second embodiment.

As shown in FIG. 4, the light separating device 21 is configured to separate the light emitted from the light emitting device 4A into the plurality of light beams and direct the light beams toward the light receiving device 5A. The number of light beams is the same as that of the light beams emitted by the light emitting elements 40 and 41, and the wavelengths of the light beams after separation correspond to the wavelengths of the light beams of the light emitting elements 40 and 41. The light separating device 21 may be a light separating element, which includes a prism, grating (reflecting diffraction grating) and the like. The fuel property sensor 1A can thus measure the transmittance over a wide range of wavelengths in low costs by such a light separating function.

The light receiving device 5A has more number of light receiving elements 50 to 53 than the light emitting elements 40, 41 of the light emitting device 4A. The light receiving device 5A includes four light receiving elements 50 to 53, which are configured to receive light beams of four predetermined wavelengths, respectively. Each of the light receiving elements 50 to 53 receives the light beams of the predetermined wavelengths and outputs a detection signal corresponding to the amount of received light beam of the predetermined wavelength, to which it is most sensitive. A light conducting plate 7A is provided between the passage 3a and the light separating device 21.

The light emitting elements 40 and 41 are both mounted on a circuit substrate 8A. The circuit substrate 8A as well as the circuit substrate 10 for the light receiving elements 50 to 53 are connected to the control unit 100 through external electric wires. A cover 9A is attached to a body 3A at a side adjacent to the light emitting device 4A. The covers 9A and 11 are made of metal or resin to protect the light emitting elements 40, 41 and the light receiving elements 50 to 53 fluid-tightly in the body 3A.

The concentration of a specific component in fuel is detected and calculated by the fuel property sensor 1A in the similar manner as in the first embodiment.

In the fuel property sensor 1A according to the second embodiment, the composite light including the plurality of predetermined wavelengths of the plurality of light beams emitted by the plurality of light emitting elements 40 and 41 is passed through fuel, and separated into the plurality of light beams to be received by the plurality of light receiving elements 50 to 53. The plurality of light emitting elements 40 and 41 output to the calculation unit 101 respective signals, each of which indicates the predetermined wavelength of its emitted light beam, as well as the amount of light emission. Each of the plurality of light receiving elements 50 to 53 outputs to the calculation unit 101 the amount of the received light beam. The calculation unit 101 calculates the transmittance of light in the specific component with respect to each wavelength based on the detected amounts of the emitted light and the received light. The calculation unit 101 calculates the concentration of the specific component based on the calculated transmittance and the characteristic of the light transmittance (specifically, data map or prediction relation), which defines the relation between the wavelength and the transmittance of light with respect to the concentration of the specific component.

Thus, the number of light emitting elements can be made less than the number of light beams of predetermined wavelengths. As a result, the number of parts of the light emitting device 4A, costs and mounting space can be reduced. The fuel property sensor 1A is therefore suitable for mounting in a vehicle, because it can be mounted in a limited space in the vehicle.

If the fuel property sensor 1A is provided with a reflective grating as the light separating device, its material is not so critical on its operation because of its reflective property. Further, the fuel property sensor 1A can be made adjustable with respect to the wavelength and less influenced by temperature.

Third Embodiment

Figure 5:
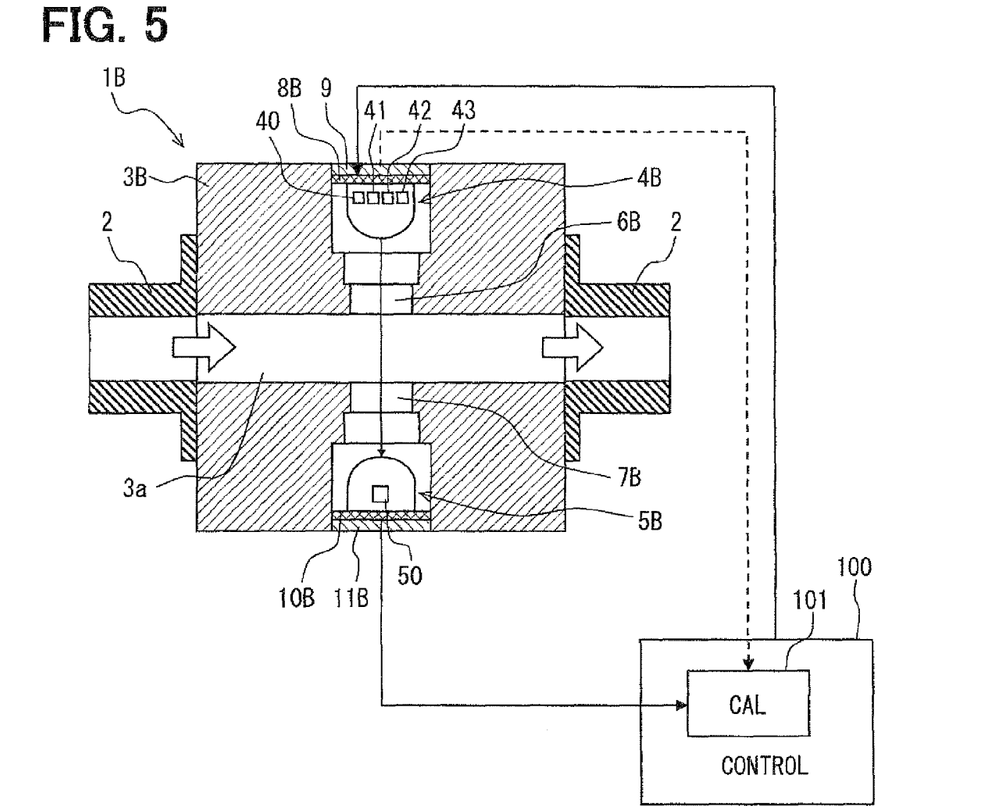
FIG. 5 is a schematic diagram showing a liquid fuel property detection apparatus according to the third embodiment of the present invention.
Figure 6:
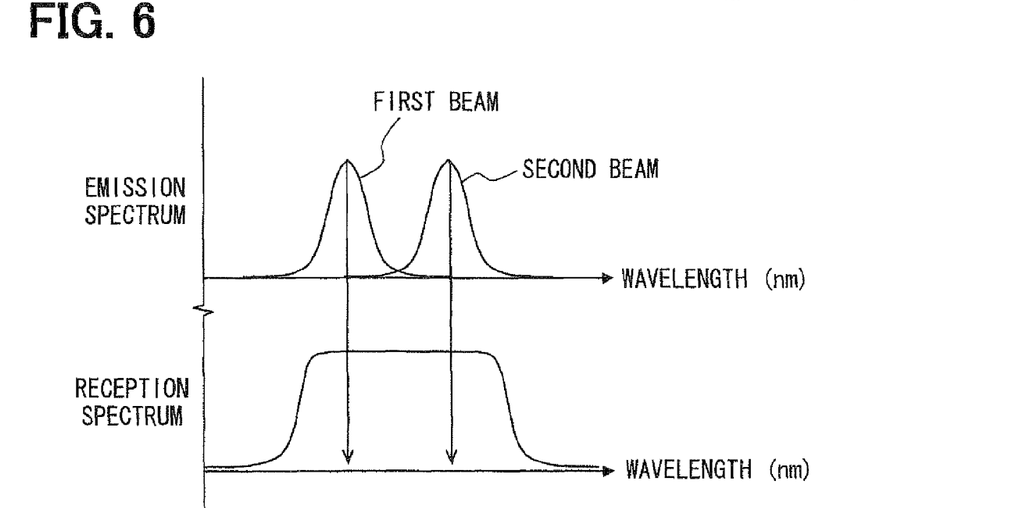
FIG. 6 is an illustration of the light emission spectrum of a light emitting device and the light reception spectrum of a light receiving device in the third embodiment.

A fuel property sensor 1B according to the third embodiment is shown in FIG. 5. A light emitting device 4B and a light receiving device 5B of the fuel property sensor 1B are configured to have the light emission spectrum and the light reception spectrum, which are shown in FIG. 6 in a simplified form. That is, in FIG. 6 only first and second light beams are shown although more light beams are emitted in the third embodiment.

Figure 7:
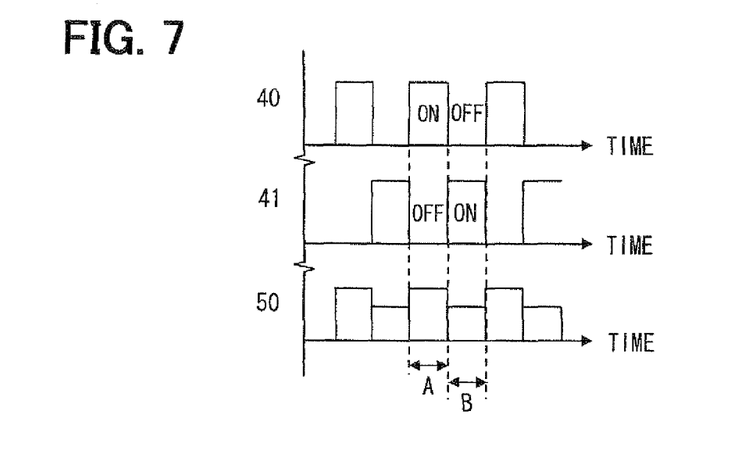
FIG. 7 is a timing diagram showing the light emission of the light emitting device and the light reception of the light receiving device in the third embodiment.

In the third embodiment, the light emitting device 4B have four light emitting elements (first light emitting element 50, second light emitting element 51, third light emitting element 52, fourth light emitting element 53) and the light receiving device 5B has only one light receiving element 50. The light emitting elements 40 to 43 emit respective light beams having different wavelengths, which are suitable for detection of the specific component. The light emitting elements 40 to 43 are driven to emit respective lights separately at different time points in the pulsed form as shown in FIG. 7. The light receiving element 50 receives the first light and the second light emitted, which are time-divided, by the light emitting elements 40 to 43.

The light beams of the light emitting elements 40 to 43 are irradiated to liquid fuel in the passage 3a through a light conducting plate 6B.

The light receiving element 50 receives sequentially the time-divided light beams of the predetermined wavelengths emitted individually and outputs to the calculation unit 101 a detection signal indicating the amount of the light beam received through a light conducting plate 7B with respect to each emitted light beam. The light emitting device 4B emits the plurality of light beams from its light emitting elements 40 to 43 (only two are shown in FIG. 6 as first and second light beams having first and second wavelengths, respectively)

toward fuel individually and the light receiving device 5B receives all the time-divided plurality of light beams by only one light receiving element 50.

All the light emitting elements 40 to 43 are mounted on a circuit substrate 8B and the light receiving element 50 is mounted on a circuit substrate 10B. The circuit substrates 8B and 10B are connected to the control unit 100 through external electric wires. A cover 9 is attached to a body 3B at a side adjacent to the light emitting device 4B and a cover 11B is attached to the body 3B at a side adjacent to the light receiving device 5B. The covers 9 and 11B are made of metal or resin to tightly protect the light emitting elements 40 to 43 and the light receiving element 50 accommodated in the body 3B from an outside environment.

The concentration of the specific component may be calculated by using the fuel property sensor 1B in the similar manner as in the first embodiment. The operation of the light emitting device 4B and the light receiving device 58 is shown in FIG. 7 as one example, assuming that the light emitting device 4B has only two (first and second) light emitting elements 40 and 41. Even in the case that the light emitting device 4B has more light emitting elements, the third embodiment will operate in the similar manner as described below.

The light emitting device 4B and the light receiving device 5B are controlled by the control unit 100. The control unit 100 drives the first light emitting element 40 and the second light emitting device sequentially. When the first light emitting element 40 is turned on by a drive voltage to emit its light beam, the second light emitting element (other light emitting element) 41 is turned off not to emit its light beam. When the second light emitting element 41 is turned on by a drive voltage to emit its light beam, the first light emitting element 40 is turned off not to emit its light beam. The light receiving device 5B outputs to the calculation unit 101 a detection signal having a voltage magnitude varying with the amount of the received light. That is, when the first light emitting element 40 is turned on (period A), the voltage magnitude of the detection signal of the light receiving device 5B corresponds to the amount of the received first light beam of the first wavelength. When the second light emitting element 41 is turned on (period B), the voltage magnitude of the detection signal of the light receiving device 5B corresponds to the amount of the received second light beam of the second wavelength.

According to the fuel property sensor 1B, the light emitting device 4B has a plurality of light emitting elements 40 to 43, which emit respective light beams having different wavelengths suitable for detection of the specific component, and the light receiving device 5B has only one light receiving element 50. The plurality of light emitting elements 40 to 43 of the light emitting device 4B are driven to emit respective light beams sequentially not to overlap one another. The light receiving element 50 of the light receiving device 5B receives the light beams emitted from the light emitting elements 40 to 43 sequentially in timed relation with the emission of the light beams by the light emitting elements 40 to 43.

According to the third embodiment, the number of the light receiving element in the light receiving device 5B is reduced in comparison to the number of the light beams of different wavelengths emitted from the light emitting device 4A. Since the liquid fuel property detection apparatus is disposed such that the fuel property sensor 1B is provided in the fuel pipe 2, the space for accommodating the sensor is normally limited and hence the sensor is required to be compact in size. The fuel property sensor 1B according to the third embodiment is therefore suited to be mounted in the limited space in a vehicle.

Fourth Embodiment

Figure 8:
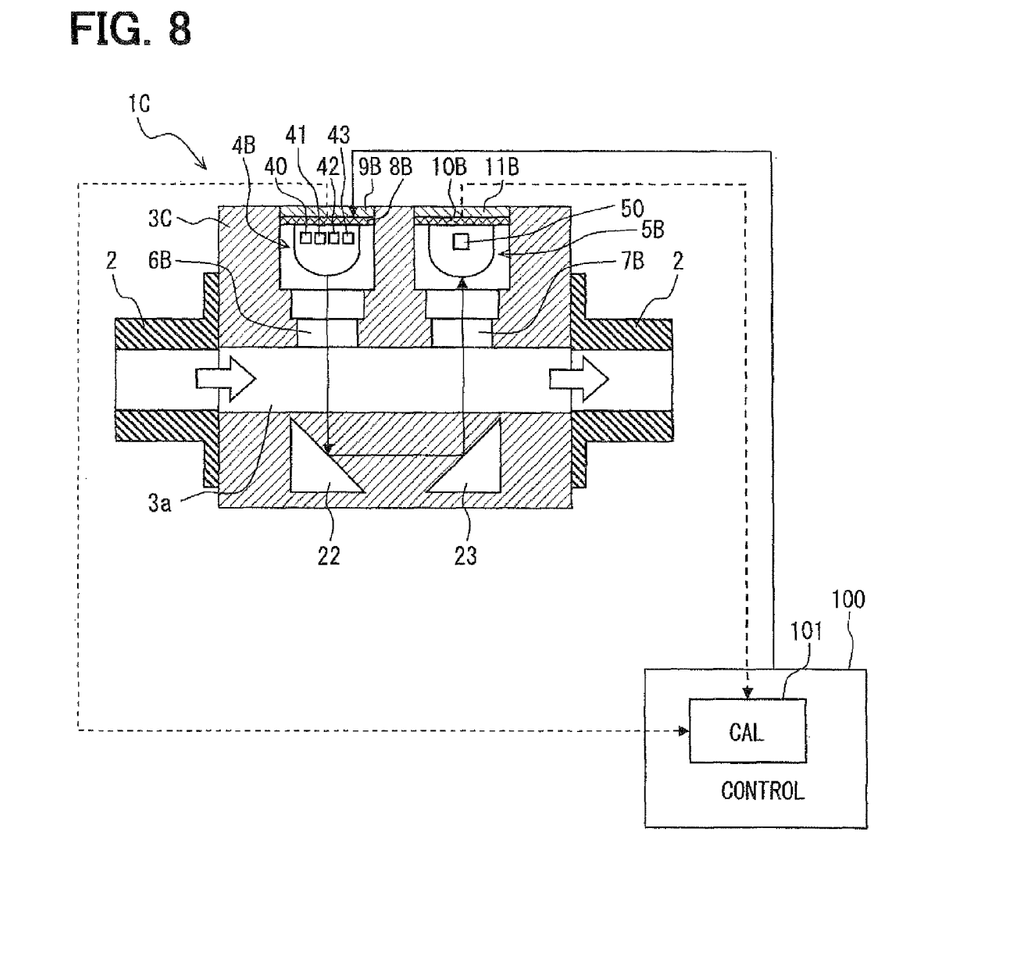
FIG. 8 is a schematic diagram showing a liquid fuel property detection apparatus according to the fourth embodiment of the present invention.

A fuel property sensor 1C according to the fourth embodiment is shown in FIG. 8. The characteristic part of the fuel property sensor 1C may also be implemented in the fuel property sensors 1, 1A and 1B of the foregoing embodiments.

As shown in FIG. 8, a light transmitting device 413 and a light receiving device 5B are both positioned at the same side (top side in the figure) relative to the fuel passage 3a. A light reflecting device, which includes a first prism 22 and a second prism 23, is positioned at the side (bottom side in the figure) opposite to the devices 4B and 5B from the fuel passage 3a. The prisms 22 and 23 are positioned to face the light emitting device 4B and the light receiving device 5B through the passage 3a, respectively. Thus, the light beams emitted from the light emitting device 4B transversely pass through the fuel in the passage 3a, reflect by the light reflecting device, and transversely pass through the fuel to the light receiving device 5B. The light transmitting elements 40 to 43 are mounted on a circuit substrate 8B and the light receiving element 50 is mounted on a circuit substrate 1013. Covers 9B and 11B are attached to a body 3C to protect the light transmitting device 4B and the light receiving device 5B from the external environment.

The light beams emitted from the light emitting device 4B are transmitted to the prism 22 through a light conducting plate 6B and fuel in the passage 3a. The prism 22 is configured and arranged to change the direction of travel path of the incident light thereof in the orthogonal direction relative to the light incident direction, that is, toward the prism 23 by reflection. The prism 23 is configured and arranged to change the direction of travel path of the incident light thereof in the orthogonal direction relative to the light incident direction, that is, toward the light receiving device 5B by reflection. The reflected light transversely passes through the fuel in the passage 3a and a light conducting plate 7B and enters the light receiving device 5B. The light beams emitted from the light emitting device 4B and the light beams reflected by the prism 23 thus travel in the opposite directions to each other.

In the fuel property sensor 1C according to the fourth embodiment, the light emitting device 4B and the light receiving device 5B are positioned at one side (top side in the figure) of the fuel passage 3a, and the light reflecting device 22, 23 are positioned at the other side (bottom side in the figure). Thus, the light reflecting device 22, 23 face the light emitting device 48 and the light receiving device 5B each other with the fuel passage 3a therebetween. As a result, the length of travel path of the light beams from the light emitting device 4B to the light receiving device 5B is more than doubled than in the foregoing embodiments, in which the light emitting device and the light receiving device are positioned at the opposite sides of the passage 3a to face each other through the passage 3a. With the lengthened light travel path, the light is attenuated more. As a result, a small change in the amount of light can be detected more readily, and the concentration of the specific component can be detected more accurately. Since both the light emitting device 4B and the light receiving device 5B are provided at the same side of the fuel passage 3a, the light travel path length can be increased without sizing the fuel property sensor 1C large. The fuel property sensor 1C is therefore suited to be mounted in the limited space in a vehicle.

Other Embodiments

The present invention is not limited to the disclosed embodiments, but may be implemented in different ways.

In the foregoing embodiments, the concentration of the specific component may be calculated by other ways in place of using the prestored equations. For example, the control unit 100 may prestore data map, which corresponds to a characteristic curve defining a relation between the wavelength of light beam and the transmittance of light beam with respect to concentrations of the specific component, so that the concentration may be calculated based on the actually calculated transmittance and the data prestored in the map form.

In the fourth embodiment, the light emitted from the light emitting device 4B reaches the light receiving device 5B by making one round-travel. The number of round-travels ma be increased to 1.5, 2 or more by increasing the light reflecting device.

In the foregoing embodiments, the light receiving element may be other elements such as a photo diode, which is different from the photo transistor.

What is claimed is:

1. A liquid fuel property detection apparatus comprising:
a passage, in which liquid fuel flows;
a light emitting device for emitting a light transversely toward the fuel in the passage, the light including a plurality of predetermined wavelengths;
a light receiving device for receiving the light including the plurality of predetermined wavelengths, the light being transmitted through the fuel; and
a calculation unit for calculating concentration of at least one specific component of aroma component, paraffin component and olefin component, which are hydrocarbon series constituent substances contained in the fuel,
wherein the calculation unit is configured to calculate the concentration of a specific component of at least one of the aroma component, the paraffin component and the olefin component based on a characteristic of reference transmittance of the light in the specific component relative to wavelength of the light and actual transmittance of the light, which is calculated from an amount of the light including the plurality of predetermined wavelengths emitted from the light emitting device and an amount of the light received by the light receiving device.

2. The liquid fuel property detection apparatus according to claim 1, wherein:
the light emitting device includes a plurality of light emitting elements, which are less in number than a plurality of light receiving elements of the light receiving device, and a light combining device for combining light beams of the plurality of light emitting elements to produce a composite light; and
a light separating device is provided for separating the composite light transmitted through the fuel into a plurality of light beams to be directed to the plurality of receiving elements.

3. The liquid fuel property sensor according to claim 1, wherein:
the light emitting device includes a plurality of light emitting elements, which are driven to emit a plurality of light beams of the predetermined wavelengths, respectively, at different time points; and
the light receiving device includes a single light receiving element, which receives the plurality of light beams individually.

4. The liquid fuel property detection apparatus according to claim 1, wherein:
the light emitting device and the light receiving device are positioned at a same side relative to the passage; and
a reflecting device is positioned at a side opposite the light emitting device relative to the passage so that the light emitted from the light emitting device is transmitted through the fuel in the passage, reflected by the light reflecting device, transmitted through the fuel in the passage again and received by the light receiving device.

5. The liquid fuel property detection apparatus according to claim 1, wherein:
the calculation unit is configured to calculate the concentration of the specific component by substituting the calculated actual transmittance for a prediction relation determined by multivariate analysis technique based on the characteristic of transmittance of the light in the specific component relative to wavelength of the light.

6. The liquid fuel property detection apparatus according to claim 1, wherein:
the plurality of predetermined wavelengths includes a wavelength, at which the reference transmittance varies most depending on a difference in the concentration of the specific component.

7. The liquid fuel property detection apparatus according to claim 6, wherein:
the plurality of predetermined wavelengths further include a wavelength, at which the reference transmittance varies least depending on the difference in the concentration of the specific component.

8. The liquid fuel property detection apparatus according to claim 1, wherein:
the plurality of predetermined wavelengths includes a wavelength, at which the reference transmittance takes a local peak value with respect to each concentration of the specific component.

* * * * *